United States Patent [19]

Cavalla et al.

[11] 4,197,241

[45] Apr. 8, 1980

[54] HEXAHYDROAZEPINE, PIPERIDINE AND PYRROLIDINE DERIVATIVES

[75] Inventors: John F. Cavalla, Isleworth; Alan C. White, Windsor, both of England

[73] Assignee: John Wyeth & Brother Limited, Maidenhead, United Kingdom

[21] Appl. No.: 961,087

[22] Filed: Nov. 15, 1978

[30] Foreign Application Priority Data

Dec. 22, 1977 [GB] United Kingdom ............... 33370/77

[51] Int. Cl.$^2$ ........................................... C07D 223/10
[52] U.S. Cl. .................... 260/239.3 R; 260/326.5 FL; 260/239 B; 260/326.8; 424/244; 424/267; 424/274; 546/222; 546/236; 546/240
[58] Field of Search ............... 260/239.3 R, 326.5 FL; 546/221

[56] References Cited

FOREIGN PATENT DOCUMENTS

| 850777 | 7/1977 | Belgium | 260/326.5 M |
| 1285025 | 8/1972 | United Kingdom | 260/239.3 R |

OTHER PUBLICATIONS

Duong et al., "Australian J. Chem." (1976) vol. 29, pp. 2651-2665.
Deslongschamps et al., "Canad. J. Chem." (1975), vol. 53, pp. 1682-1683.
Hullot et al., "Canad. J. Chem." (1976), vol. 54, pp. 1098-1104.
Kugita et al., "J. Med. Chem." (1965), vol. 8, pp. 313-316.
Cavalla et al., "J. Med. Chem." (1965), vol. 8, pp. 316-326.
Tamura, "J. Med. Chem." (1970), vol. 20, pp. 709-714.

*Primary Examiner*—Alan L. Rotman
*Assistant Examiner*—Robert T. Bond
*Attorney, Agent, or Firm*—Arthur E. Wilfond

[57] ABSTRACT

The invention concerns novel 2-oxo-hexahydroazepine, -piperidine and -pyrrolidine derivatives of formula (I) and their aromatized derivatives of formula (II)

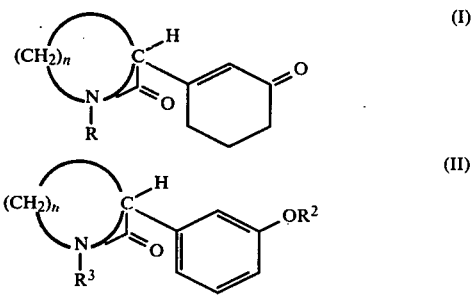

where n is 2, 3 or 4, R is hydrogen, lower alkyl or aryl(lower)alkyl, $R^2$ is hydrogen, lower alkyl or aryl(lower)alkyl and $R^3$ is hydrogen, lower alkyl, aryl(lower)alkyl, lower alkenyl or lower alkynyl. The compounds are useful as intermediates for preparing 3,3-disubstituted -hexahydroazepine, -piperidine and -pyrrolidine compounds having pharmacological activity, particularly analgesic activity.

19 Claims, No Drawings

HEXAHYDROAZEPINE, PIPERIDINE AND PYRROLIDINE DERIVATIVES

The invention relates to hexahydroazepine, piperidine and pyrrolidine derivatives. More particularly the invention relates to certain novel 2-oxo-hexahydroazepine, -piperidine and -pyrrolidine derivatives, to a novel process for preparing the novel derivatives and to the use of the novel derivatives in preparing 3,3-disubstituted-hexahydroazepine, -piperidine, and -pyrrolidine derivatives.

Various 3,3-disubstituted hexahydroazepines, -piperidines and -pyrrolidines are known to have pharmacological activity, particularly analgesic activity. For example, analgesic 2-unsubstituted-3,3-disubstituted-hexahydroazepines, such as meptazinol, are disclosed in U.K. specification No. 1,285,025. Profadol and related 3,3-disubstituted-pyrrolidines are described in J.Med.Chem. 1965, 8, 316 and Belgian Pat. No. 850,777 while myfadol and related 3,3-disubstituted-piperidines are described in J.Med.Chem, 1965, 8, 313. The known processes for preparing the 3,3-disubstituted-hexahydroazepines, -piperidines and -pyrrolidines are expensive and it is an object of the present invention to provide novel intermediates which may be easily prepared by a novel process from readily available starting materials and which can be converted into the desired 3,3-disubstituted-hexahydroazepines, -piperidines and pyrrolines such that the overall process for preparing the final products is generally more economic than the known processes.

The novel compounds provided by the invention are 2-oxo-hexahydroazepine, -piperidine and -pyrrolidine derivatives of the general formula (I)

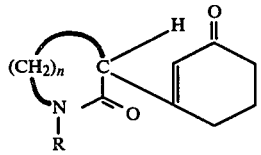

(I)

wherein n is 2, 3 or 4 and R is hydrogen, lower alkyl or aryl(lower)alkyl.

The term "lower" as used herein means that the radical referred to contains 1 to 6 carbon atoms. The radical preferably contains 1 to 4 carbon atoms. For example when R is lower alkyl, the radical may be, for example, methyl, ethyl, propyl or butyl. When R is aryl(lower)alkyl, the radical is preferably a phenyl(lower)alkyl radical such as phenethyl or benzyl; the phenyl group may be substituted by, for example, one or more substituents such as halogen, alkoxy, trifluoromethyl or other substituents common in medicinal chemistry.

The compounds of general formula (I) may be converted by procedures described herinafter to their aromatised derivatives of general formula (II)

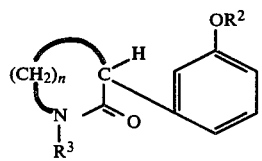

(II)

where n is as defined above, $R^2$ is hydrogen, lower alkyl or aryl(lower)alkyl and $R^3$ is hydrogen, lower alkyl, aryl(lower)alkyl, lower alkenyl or lower alkynyl. The compounds of general formula (II) are novel compounds and are also provided by this invention.

Where $R^3$ is lower alkenyl or lower alkynyl it is to be understood that the double or triple bond is not in the 1-position of the alkenyl or alkynyl radical; examples of suitable alkenyl and alkynyl radicals are allyl, propargyl, 3,3-dimethylallyl and 1-methyl-2-propynyl.

The compounds of general formula (II) may be prepared by aromatising and optionally O-(lower)alkylating or O-aryl(lower)alkylating the compounds of general formula (I) to give a compound of general formula (II) in which $R^3$ is hydrogen, lower alkyl or aryl(lower)alkyl and, if desired "N-alkylating" a compound of general formula (II) in which $R^3$ is hydrogen to give a compound of general formula (II) in which $R^3$ is lower alkyl, aryl(lower)alkyl, lower alkenyl or lower alkynyl.

By "N-alkylating" is meant introducing onto the nitrogen atom of the heterocyclic ring a lower alkyl, aryl(lower)alkyl, lower alkenyl or lower alkynyl radical. A compound of formula (I) may be aromatised to a compound of formula (II) in which $R^2$ is hydrogen by treatment with cupric halide (e.g. cupric bromide or cupric chloride), in the presence or absence of lithium halide. The reaction may be carried out in a solvent such as tetrahydrofuran or, preferably, acetonitrile. Alternatively a compound of general formula (I) may be aromatised to a compound of general formula (II) by treatment with bromine, for example, in a solvent such as chloroform, methylene dichloride or carbon tetrachloride. Preferably not more than about 1 mole of bromine is used per mole of compound of general formula (I). Alternatively, a compound of formula (I) may be aromatised and O-(lower)alkylated to a compound of formula (II) in which $R^2$ is lower alkyl by treatment with bromine in presence of a lower alkanol (for example, in a solvent such as benzene, cyclohexane or acetonitrile) or by treatment with a brominating agent such as N-bromosuccinimide in, for example, a solvent such as chloroform, methylene dichloride or carbon tetrachloride containing a lower alkanol.

We have found that the compounds of general formula (I) can be prepared by a novel process from readily available starting materials. Accordingly in a further aspect the invention provides a process for preparing a compound of general formula (I) which comprises reacting a cyclohexene derivative of general formula (IV)

$$\underset{Q}{\overset{O}{\parallel}}$$

(IV)

where Q is a hydrolysable protecting group such as lower alkoxy (preferably methoxy, ethoxy or i-propyloxy), benzyloxy, trialkyl-, triaryl- or tri-aralkyl-silyloxy(e.g. trimethylsilyloxy) with an anion or dianion of a lactam of general formula (V)

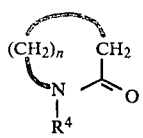

(V)

where n is as defined above and R⁴ is hydrogen, lower alkyl, aryl(lower)alkyl or trialkyl-, triaryl- or triarylalkyl-silyl (e.g. trimethylsilyl) and subjecting the product to hydrolysis. The lactam of general formula (V) can form its dianion when R⁴ is hydrogen and an anion when R⁴ is other than hydrogen. For example when R⁴ is other than hydrogen the anion of the lactam of general formula (V) may be formed in situ by reacting the lactam with an alkyl lithium (e.g. tertiary butyl lithium) or with a compound of general formula MA [where M is —MgX (where X is chlorine, bromine or iodine), sodium, potassium or lithium and A is a secondary amine radical]. When M is sodium, potassium or lithium the compound MA is a metal amide and is itself preferably formed in situ by reacting a metal compound MR⁵ (where M is sodium, potassium or lithium and R⁵ is alkyl, aryl or aralkyl) with a secondary amine. The secondary amine may be a dialkylamine, e.g. diethylamine, di-isopropylamine, di-tertiarybutylamine, di-n-decylamine, dicyclohexylamine, N-t-amyl-N-t-butylamine, N-isopropyl-N-cyclohexylamine or N-(1'-ethylcyclohexyl)-1,1,3,3-tetramethylbutylamine or a cyclic compound, e.g. piperidine or 2,2,6,6-tetramethylpiperidine. A preferred metal amide is lithium diisopropylamide. The anion of the lactam in which R⁴ is other than hydrogen may be prepared by reacting the lactam with a Grignard reagent (preferably isopropylmagnesium bromide) or with a dialkylamino magnesium halide e.g. bromomagnesiumdiisopropylamide. When R⁴ is hydrogen the dianion of the lactam may be prepared by reacting the lactam with an alkyl lithium (e.g. tert.butyl lithium or butyl lithium) or with an alkali metal hydride (e.g. sodium hydride) followed by an alkyl lithium (e.g. butyl lithium).

The product of the reaction of the anion or dianion of the lactam of general formula (V) and the cyclohexene derivative (IV) is preferably not isolated but hydrolysed in situ to give the compound of general formula (I). If R⁴ in the compound of general formula (V) is a tri-alkyl-, tri-aryl- or tri-aralkylsilyl group, this group is removed by the hydrolysis to give a compound of general formula (I) in which R is hydrogen.

The compounds of formula (I) and their simple derivative of formula (II) are useful as intermediates for preparing pharmacologically active hexahydroazepine, piperidine and pyrrolidine derivatives. For example, compounds (I) can be aromatised (and optionally O-(lower)alkylated or O-aryl(lower)alkylated) as mentioned above to give compounds (II). The compounds of general formula (II) in which R³ is hydrogen can also be "N-alkylated" as mentioned above; it is preferable to N-alkylate a compound in which R² is lower alkyl or aryl(lower)alkyl. Compounds of formula (II) in which R² is hydrogen can be O-(lower)alkylated or O-aryl(lower)alkylated to give compounds in which R² is lower alkyl or aryl(lower)alkyl. The compounds of formula II can be alkylated in the 3-position with, for example, a lower alkyl group to give 3,3-disubstituted compound of formula

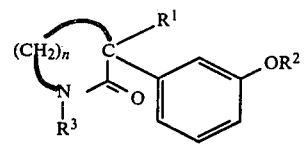

where n, R² and R³ have the meanings given above and R¹ is lower alkyl. The 3,3-disubstituted compounds can be reduced to give a 2-unsubstituted-3,3-disubstituted-hexahydroazepine, -piperidine or -pyrrolidine derivative. An embodiment of this route for preparing 2-unsubstituted-3,3-disubstituted-hexahydroazepines is illustrated, by way of example, in the reaction scheme below:

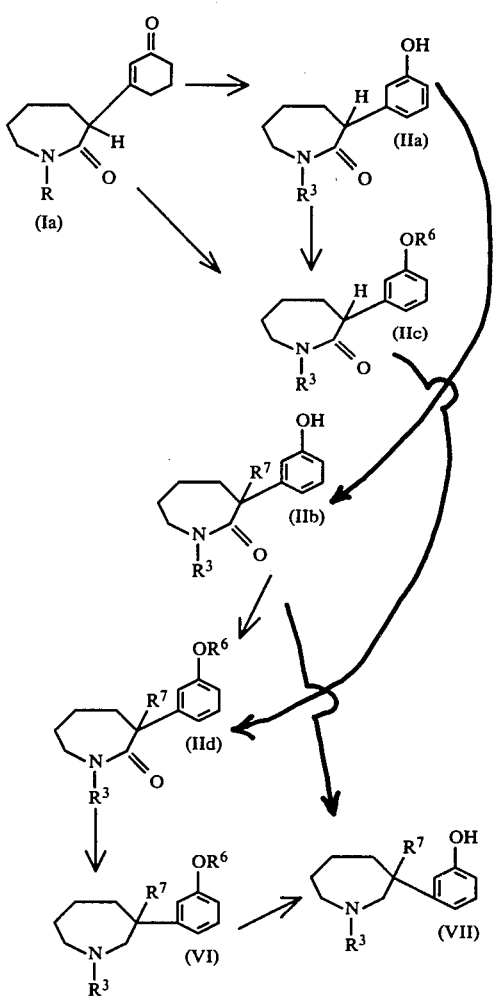

In this reaction scheme R and R³ have the meanings given above, R⁶ is lower alkyl or aryl(lower)alkyl and R⁷ is lower alkyl. Compounds (Ia) can be aromatised to compounds (IIa) by the procedures described above or alternatively compounds (Ia) can be aromatised and O-(lower)alkylated to compounds (IIc) respectively by the procedure described above. If desired compound (IIa) can be etherified to compound (IIc) by treatment with a (lower) alkylating agent, e.g. dimethyl sulphate or with an aryl(lower)alkylating agent such as benzyl chloride. Either compound IIa or compound IIc can be C-(lower)alkylated to compound IIb or compound IId respectively. The C-(lower)alkylation can, for example, be carried out by reacting compound IIa or IIc with an alkyl halide (e.g. an alkyl bromide) in presence of a strong base, such as sodium hydride, sodamide or a metal amide $M^1A$ (where A is as defined above and $M^1$ is sodium, potassium or lithium). The metal amide, such as lithium diisopropylamide may be formed in situ. Under some conditions compound IIa may be both C- and O-alkylated to a compound of formula IId. If $R^3$ in the compound IIa is hydrogen then the N-atom should be alkylated (using a base such as for example sodium hydride in toluene) or benzylated before carrying out the C-(lower)alkylation process. The compounds IIb and IId can be reduced to the compounds VII and VI respectively as disclosed in our UK patent specification No. 1,285,025. For example, the reduction can be carried out with a hydride transfer agent, e.g. lithium aluminium hydride. If desired compound VI can be converted to compound VII by ether cleavage, e.g. with hydrogen bromide or boron tribromide, as described in the above mentioned UK specification No. 1,285,025.

Compounds VI and VII are disclosed in UK specification No. 1,285,025 as having pharmacological activity, particularly analgesic activity. A particularly important analgesic compound is that of formula VII in which $R^3$ is methyl and $R^7$ is ethyl. This compound is meptazinol. The present invention provides a novel process for preparing such compounds in good yield from readily available starting materials. For example, the starting materials of formula V in which n is 4 are readily available derivatives of caprolactam.

The processes shown in the reaction scheme can be subject to various modifications. For example, the alkyl halides used in the C-alkylation of compounds IIa and IIc can be replaced by other active halogen compound to give compounds corresponding to VI and VII in which the 3-(lower)alkyl radical is replaced by an alkyl radical containing a functional group; if this functional group is reducible it may be further modified during the subsequent reduction step. In a further modification the group in the 1-position of the intermediate compounds may be removed to give a N-H-derivative which may subsequently be alkylated, as for example, described in specification No. 1,285,025, to give a product having a different 1-substituent. Analogous reactions to those described above in connection with the Reaction Scheme and the modifications can be carried out with compounds I and II in which n is 2 or 3 to give analogous 2-unsubstituted-3,3-disubstituted-piperidines and -pyrrolidines having pharmacological activity such as profadol and related pyrrolidines described in J. Med. Chem., 1965, 8, 316 and Belgian Pat. No. 850,777 and myfadol and related piperidines described in J. Med. Chem., 1965, 8, 313.

Compounds of general formula II can be prepared by alternative methods. One method is illustrated below:

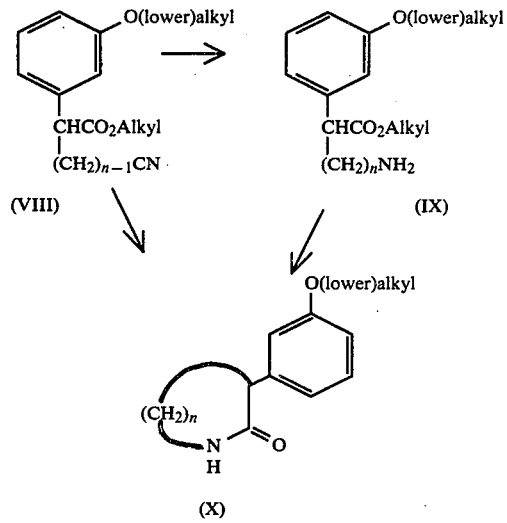

In the above formulae n has the meaning given hereinbefore. In this process a nitrile ester of general formula VIII is reduced either directly to the cyclised compound of formula X or to the open chain compound IX which can be cyclised to the compound X. The reduction can be carried out by catalytic hydrogenation, e.g. at a temperature up to about 80° C. (for example with hydrogen in presence of palladium on charcoal at about room temperature in a solvent such as methanol containing sulphuric acid and under a pressure of about 60 p.s.i.) or at a temperature above about 100° C. (e.g. with hydrogen in the presence of Raney nickel at temperatures of about 100° to 150° C. in a solvent such as cyclohexane and under pressures of about 800 to 1200 p.s.i.). Low temperature reduction tends to give the open chain compound IX while higher temperature reduction tends to give compound X. The open chain compound IX may be cyclised to the compound X, e.g. by heating in a solvent (e.g. refluxing xylene or toluene). The compounds X are compounds of formula II in which $R^3$ is hydrogen. Compounds X can be converted into the compounds II in which $R^3$ is lower alkyl or aryl(lower)alkyl by selectively N-alkylating (including N-arylakylating) them with alkylating agents such as alkyl halides in the presence of a base.

The following examples illustrate the invention:

EXAMPLE 1

Hexahydro-3-(3-methoxyphenyl)-2H-azepin-2-one 2-(3-Methoxyphenyl)-5-cyanopentanoic acid methyl ester (10 g) was reduced at 60 p.s.i. in methanol (100 ml) containing conc. sulphuric acid (7.2 ml) and 10% palladium charcoal (2.2 g). Uptake ceased when 2 moles of hydrogen had been taken up. The catalyst was filtered off, methanol removed under reduced pressure affording an oil. The oil was poured into water, basified with conc. ammonium hydroxide, extracted into ether, the combined ether washings dried over magnesium sulphate and evaporated to an oil.

The oil (11 g) was heated under reflux in xylene for six days. The xylene was removed under reduced pressure affording an oil which gave pale yellow crystals of the title product from ethyl acetate (2.72 g), m.p. 116°–117° C. A further 894 mg of crystals were obtained by distilling the residue and crystalling the resulting oil from ethyl acetate.

Analysis: Found: C, 71.35; H, 7.94; N, 6.7%: $C_{13}H_{17}NO_2$ requires: C, 71.2; H, 7.8; N, 6.4%.

EXAMPLE 2

Hexahydro-3-(3-methoxyphenyl)-1-methyl-2H-azepin-2-one

Hexahydro-3-(3-methoxyphenyl)-2H-azepin-2-one (2.2 g) in dry toluene (40 ml) was added dropwise to a stirred suspension of sodium hydride (0.62 g, 0.015 mole of 50% dispersion in oil, pre-washed with dry light petroleum (b.p. 40°–60°). After stirring and heating at 60° for 1 hour the reaction was cooled to 5° C. and methyl iodide (1.9 ml, 2.5 g, 0.02 mole) was added rapidly. After stirring at ambient temperature for 20 hours acetic acid and water were added. The aqueous layer was separated and washed with toluene. Toluene extracts were washed with water, dried over anhydrous magnesium sulphate and evaporated to an oil. Oil was recrystallised from ethylacetate light petroleum (b.p. 60°–80°) affording 1.95 g (83%) of hexahydro-(3-(3-methoxyphenyl)-1-methyl-2H-azepin-2-one, in several crops, m.p. 74°–5° C.

Analysis: C, 72.4; H, 8.5; N, 5.7%: $C_{14}H_{19}NO_2$ requires: C, 72.1; H, 8.2; N, 6.0%.

EXAMPLE 3

Hexahydro-1-methyl-3-(3-oxocyclohexen-1-yl)-2H-azepin-2-one

Diisopropylamine (12.14 g, 17.0 ml) in dry tetrahydrofuran (THF 20 ml) was added dropwise to a stirred cooled (−10° C.) solution of butyl lithium (86 ml of 1.4 molar solution in hexane) under nitrogen. After 10 minutes Gilman test was negative. 1-Methylcaprolactam (14.19 g) in THF (20 ml) was added, also at −10° C. Reaction was stirred for 10 minutes at 0° C. and 3-methoxy-2-cyclohexenone (12.6 g, 0.1 mole) in THF (20 ml) was added. The mixture was allowed to warm to room temperature and stirred at room temperature for 1.5 hours, then cooled to −10° C. and decomposed by addition of 2 N HCl (125 ml) rapidly but not allowing temperature to exceed 0° C. The mixture was stirred at room temperature for 30 minutes. The aqueous layer was separated and extracted with dichloromethane. The combined organic extracts were dried over anhydrous magnesium sulphate and evaporated to an oil which crystallised from toluene-light petroleum (b.p. 60°–80° C.) affording the title compound (18.99 g), m.p. 109°–110° C.

Analysis: Found: C, 70.65; H, 8.6; N, 6.1% $C_{13}H_{19}NO_2$ requires C, 70.6; H, 8.65; N, 6.3%

EXAMPLE 4

Hexahydro-3-(3-hydroxyphenyl)-1-methyl-2H-azepin-2-one

Hexahydro-b 1-methyl-3-(oxocyclohexen-1-yl)-2H-azepin-2-one (11.1 g) in acetonitrile (250 ml) was stirred overnight with a mixture of copper (II) bromide (22.3 g) and lithium bromide (4.3 g). The acetonitrile was removed under reduced pressure and the dark residue suspended in sodium hydroxide solution (2 N, 200 ml). The solution was filtered, the precipitate washed with water and the filtrate acidified with conc. hydrochloric acid. The precipitated title phenol was filtered and washed with water affording 8.62 g of off-white powder m.p. 185°–187° C. A second crop of 900 mg, m.p. 188°–191° C. was obtained by extracting the mother liquors with chloroform. The product was purified by recrystallising from ethyl acetate or ethyl acetate/methanol to give pure product, m.p. 192°–193° C.

Analysis: Found: C, 71.1; H, 8.0; N, 6.4%; $C_{13}H_{17}NO_2$ requires C, 71.2; H, 7.8; N, 6.4%.

EXAMPLE 5

Hexahydro-3-(3-methoxyphenyl)-1-methyl-2H-azepin-2-one

Hexahydro-3-(3-hydroxyphenyl)-1-methyl-2H-azepin-2-one (21.9 g) was dissolved in 2 M sodium hydroxide solution (100 ml) and dimethyl sulphate (18.3 g, 14.5 ml) added. The reaction mixture was stirred at room temperature for 10 minutes then seeded. The product crystallised after leaving at 0° C. for 3 hours. The product was filtered, washed with water and dried affording 16.99 g of title compound as off-white powder m.p. 73°–74° C., identical to that obtained in Example 2.

A further 1.69 g of the required material was obtained by treating the aqueous mother liquors with 2 M sodium hydroxide (50 ml) and dimethyl sulphate (7.25 ml).

EXAMPLE 6

3-Ethyl-hexahydro-3-(3-methoxyphenyl)-1-methyl-2H-azepin-2-one

Hexahydro-3-(3-methoxyphenyl)-1-methyl-2H-azepin-2-one (4.66 g) in dry toluene (25 ml) was added dropwise to a stirred suspension of sodium amide (1.0 g) in dry toluene (50 ml). The reaction mixture was heated to reflux, ammonia was evolved and the reaction mixture became red. After refluxing for 2 hours dry tetrahydrofuran (20 ml) was added, the mixture cooled and ethyl iodide (3.7 g) added. A white precipitate was formed and the red colour rapidly disappeared. The reaction mixture was heated under reflux for 2 hours, cooled and decomposed by the addition of water. The aqueous phase was separated and the organic layer washed with saturated sodium chloride solution, dried over anhydrous magnesium sulphate and evaporated affording an oil which crystallised from diisopropyl ether to give the title compound (3.29 g), m.p. 62°–64° C.

Analysis: Found: C, 73.5; H, 9.0; N, 5.15%: $C_{16}H_{23}NO_2$ requires C, 73.5; H, 8.9; N, 5.4%.

EXAMPLE 7

3-Ethyl-hexahydro-3-(3-methoxyphenyl)-1-methyl-1-H-azepine

3-Ethyl-hexahydro-3-(3-methoxyphenyl)-1-methyl-2H-azepin-2-one (5.52 g) in anhydrous ether (100 ml) was added dropwise to a stirred suspension of aluminium lithium hydride (1.5 g) in anhydrous ether (50 ml). The reaction was heated under reflux for 3 hours.

A further portion of aluminium lithium hydride (1.0 g) was added and heating continued for a further 2 hours. After cooling, the reaction mixture was decomposed by the successive addition of water (3 ml), 15% sodium hydroxide (3 ml) and water (6 ml). The granular precipitate was filtered and the precipitate washed with ether. The combined filtrate and ether washings were extracted with 2 M hydrochloric acid (3×25 ml). The combined acid washings were basified with 15 M aqueous ammonium hydroxide and extracted with ether. After drying over anhydrous magnesium sulphate the solvent was removed to leave 3.98 g of title compound as a colourless oil 98% pure by gas/liquid chromatography and identical to the material prepared by an alternative route. [The product is converted to 3-ethyl-hexahydro-3-(3-hydroxyphenyl)-1-methyl-1H-azepine by treatment with hydrobromic acid according to the procedure described in U.K. specification No. 1,285,025.]

EXAMPLE 8

3-Ethylhexahydro-3-(3-hydroxyphenyl)-1-methyl-2H-azepin-2-one

Butyl lithium (77 ml of a 1.4 molar solution in hexane) was added to a solution of diisopropylamine (14.8 ml) in dry tetrahydrofuran (20 ml) at −10° C. under nitrogen. The mixture was stirred at −10° C. for ten minutes and finely powdered hexahydro-3-(3-hydroxyphenyl)-1-methyl-2H-azepin-2-one (11 g) was added. Tetrahydrofuran (500 ml) was added and the mixture heated under reflux for 3 hours. After cooling, ethyl iodide (8.2 g) was added and the mixture again heated under reflux for 3 hours. Water (20 ml) was then cautiously added to the cooled solution and the mixture evaporated to a brown residue. After dissolving in water the mixture was extracted with dichloromethane and the dichloromethane extracted in turn with 2 M sodium hydroxide. The aqueous and sodium hydroxide washings were combined and acidified with concentrated hydrochloric acid. The precipitated solid was filtered, washed with water, dried and recrystallised from ethyl acetate, affording 8.72 g of the title compound as white crystals, m.p. 178°–180° C.

Analysis: Found: C, 72.55; H, 8.6; N, 5.3%. $C_{15}H_{21}NO_2$ requires C, 72.8; H, 8.6; N, 5.7%.

EXAMPLE 9

3-Ethyl-hexahydro-3-(3-hydroxyphenyl)-1-methyl-2H-azepine

A solution of 3-ethylhexahydro-3-(3-hydroxyphenyl)-1-methyl-2H-azepin-2-one (1.5 g) in dry tetrahydrofuran was added to a stirred suspension of aluminium lithium hydride (0.48 g) and heated under reflux for 5 hours. The reaction mixture was cooled and decomposed by the addition of water and the precipitate filtered. The precipitate was washed with tetrahydrofuran and the combined filtrate and washings evaporated to a solid. The solid was dissolved in water and ammonium chloride added. The precipitated oil was extracted with dichloromethane, dried over anhydrous magnesium sulphate and evaporated to leave a solid which was recrystallised from acetonitrile to give 0.91 g of the title compound, m.p. 127.5°–133° C., identical with material prepared by an alternative route described in U.K. specification No. 1,285,025.

EXAMPLE 10

1-Methyl-3-(3-oxocyclohexen-1-yl)-2-piperidone n-Butyllithium (1.4 M in hexane, 120 ml) was treated at 20° C. under dry nitrogen with diisopropylamine (27 ml, 19.2 g) in dry ether (25 ml). The mixture was stirred for 10 minutes at 20° C. after completion of the addition and then 1-methyl-2-piperidone (20 g) in ether (25 ml) was added dropwise over 10 minutes. The mixture was stirred for a further 10 minutes, and then 3-isopropoxy-2-cyclohexenone (19.4 g) in ether (25 ml) was added dropwise over 10 minutes. The mixture was stirred at 20° C. for a further 2 hours and was then hydrolysed by the addition, dropwise at first, of a mixture of conc. hydrochloric acid (50 ml) and water (50 ml). The mixture was cooled in a water bath during the acidification to moderate the reaction. The mixture was cooled to room temperature (from 35° C.) and the organic phase was separated and dried (MgSO₄). Removal of the solvent left a mobile yellow oil (0.63 g). The aqueous phase was extracted exhaustively with chloroform (10×40 ml) and the combined extracts were washed with water (100 ml), and saturated aqueous sodium chloride solution (100 ml), and dried (MgSO₄). Evaporation left a pale green oil (25.79 g). The two fractions were combined and distilled, giving two fractions A, bp<120° C./1 mm (4.6 g), colourless, mobile liquid; and B, bp 150° C.–164° C./0.07 mm (14.46 g), yellow oil solidifying to a light yellow mass, mp 41°–62° C. Fraction A was identified by IR as slightly impure 1-methyl-2-piperidone (23% recovery), while fraction B was identified by IR and NMR as the title compound.

EXAMPLE 11

3-(3-Hydroxyphenyl)-1-methyl-2-piperidone

1-Methyl-3-(3-oxocyclohexen-1-yl)-2-piperidone (3.5 g) was refluxed in acetonitrile (100 ml) in the presence of lithium bromide (1.4 g) and cupric bromide (7.6 g) for 0.5 hours. The acetonitrile was evaporated to give a gum, to which 2 N sodium hydroxide (100 ml) was added, the solution filtered, conc. HCl (30 ml) added to the filtrate, the aqueous extracted with chloroform, dried (MgSO₄) and evaporated to give an oil, which on standing overnight, at 0° C., in hexane gave a yellow solid. This was collected, washed with ether then acetone to give the title compound as the quarter hydrate, a colourless solid (0.50 g) m.p. 111°–114° C.

Analysis: Found: C, 69.1; H, 7.27; N, 7.11%: $C_{12}H_{15}NO_2 \cdot H_2O$ requires C, 68.7; H, 7.45; N, 6.68%.

EXAMPLE 12

Hexahydro-1-methyl-3-(3-oxocyclohexen-1-yl)-2H-azepin-2-one

2-Bromopropane (12.3 g) was added to suspension of magnesium (2.43 g) in ether (50 ml) at such a rate to maintain gentle reflux and the mixture was stirred 30 minutes after addition was complete. Diisopropylamine (14 ml) was then added dropwise and the mixture stirred until the Gilman test showed negative (about 1 hour). N-methylcaprolactam (12.7 g) was added dropwise (exothermic). After addition of the N-methylcaprolactam, stirring became difficult due to separation of a sticky solid, which however redissolved on addition of THF (50 ml). After the addition was complete the reaction mixture was stirred for 30 minutes then treated dropwise with 3-isopropoxy-2-cyclohexenone (16.4 g) (exothermic) and stirred overnight. The reaction mixture was poured onto 2 N aq HCl (250 ml) and stirred for 30 minutes. Dichloromethane (300 ml) was added and the layers separated. The aqueous layer was extracted with dichloromethane (2×300 ml) and the combined organic phases dried (MgSO₄). Removal of the solvents under reduced pressure followed by recrystallisation of the residue from ethyl acetate gave the title compound (13.2 g) identical with the product of Example 3.

EXAMPLE 13

1-Methyl-3-(3-oxocyclohexen-1-yl)-2-pyrrolidone n-Butyllithium (1.4 Molar in hexane, 190 ml) was treated dropwise over 10 minutes under dry nitrogen with diisopropylamine (30.3 g) in dry ether (50 ml), with external water cooling to maintain the reaction temperature below 25° C. After a further 10 minutes, freshly distilled dry 1-methyl-2-pyrrolidone (27.72 g) in dry ether (25 ml) was added dropwise over 15 minutes, and the suspension was stirred for a further 20 minutes at 20° C. 3-Isopropoxy-2-cyclohexenone (31 g) in ether (25 ml) was added to the mixture over 15 minutes, the suspended solid dissolving during the addition. The mixture was stirred for a further 2 hours at 20° C. and was then cooled in ice and treated, dropwise at first, with a mixture of conc. hydrochloric acid (100 ml) and water (100 ml). After a further 10 minutes the phases were separated and the organic phase was discarded. The aqueous phase was extracted with chloroform (10×50 ml) and the combined extracts were washed with water (100 ml) and saturated aqueous sodium chloride solution (100 ml) and dried (MgSO$_4$). Evaporation of the solvent gave an initially colourless oil which darkened in air to a clear red colour (37.82 g). Distillation of the oil gave the title compound as a pale yellow liquid which solidified on seeding to a yellow mass (32.75 g), bp 161° C./0.035 mm–165° C./0.07 mm, m.p. 42°–46° C.

EXAMPLE 14

3-(3-Hydroxyphenyl)-1-methyl-2-pyrrolidone

1-Methyl-3-(3-oxocyclohexen-1-yl)-2-pyrrolidone (9.24 g), cupric bromide (21.39 g) and lithium bromide (4.16 g) were heated to reflux in acetonitrile (50 ml) for 1 hour. The resulting dark solution was evaporated to dryness and the residue was treated with 2 N sodium hydroxide solution (100 ml). The resulting orange precipitate was removed by filtration and washed with 2 N sodium hydroxide (10 ml) and water (25 ml). The alkaline filtrate and washings were combined and extracted with dichloromethane (3×50 ml) to remove unreacted starting material. The dark aqueous phase was then acidified with conc. hydrochloric acid (25 ml) and extracted with chloroform (4×50 ml). The combined, dried (MgSO$_4$) extracts were evaporated, leaving a dark gum (8.85 g) which crystallised on seeding and dilution with a little ethyl acetate to a brown crystalline mass (7.8 g, 86.1%), m.p. 95°–115° C. This material was crystallised from ethyl acetate/80°–100° petrol, giving the title compound as pale buff crystals (5.12 g), m.p. 123°–124° C. (decomp.).

EXAMPLE 15

3-(3-Hydroxyphenyl)-1-methyl-3-(1-propyl)-2-pyrrolidone

Lithium diisopropylamide was prepared under nitrogen at room temperature from n-butyllithium (1.4 M in hexane, 16 ml) and diisopropylamine (2.8 ml, 2.02 g). A solution of 3-(3-hydroxyphenyl)-1-methyl-2-pyrrolidone (1.71 g) in THF (50 ml) was added and the resulting suspension was stirred for 1 hour at room temperature. 1-Iodopropane (0.95 ml, 1.63 g) was then added in one lot, when the acid immediately dissolved. The mixture was warmed over 2 hours to reflux, held at reflux for 30 minutes, cooled, and treated with water (20 ml). Organic solvents were removed under reduced pressure and the residual aqueous phase was diluted with water (20 ml), and extracted with dichloromethane (2×50 ml). The lower emulsion phases were separated, combined, and back-extracted with water (3×10 ml). The dichloromethane phase was dried (MgSO$_4$) and evaporated, leaving impure title compound as a brown gum which partially crystallised (0.3 g). The aqueous phases were combined with the original aqueous phase (pH>12) and acidified with conc. hydrochloric acid to pH<1. The precipitated yellow gum was extracted into dichloromethane (4×25 ml) and the combined extracts were dried (MgSO$_4$) and evaporated, leaving a brown gum which crystallised on trituration with a little ethyl acetate (2.04 g). This material was crystallised, after charcoal treatment in ethyl acetate and removal of the solvent, from cyclohexane-toluene (about 1:1 v/v) to give 3-(3-hydroxyphenyl)-1-methyl-3-(1-propyl)-2-pyrrolidone as ochre crystals (0.91 g), m.p. 75.5°–76.5° C.

Analysis: Found: C, 72.2; H, 8.4; N, 6.2%: C$_{14}$H$_{19}$NO$_2$ requires C, 72.1; H, 8.2; N, 6.0%.

EXAMPLE 16

Hexahydro-3-(3-oxocyclohexen-1-yl)-2$\underline{H}$-azepin-2-one

Lithium diisopropylamide, prepared by treating diisopropylamine (45.3 ml) with 1.4 M butyl lithium in hexane (231 ml) at −10° C. under nitrogen, was treated at −60° C. with 1-trimethylsilylhexahydro-2H-azepin-2-one (63.7 g) in dry THF (50 ml). The white suspension was treated after 20 minutes with a solution of 3-methoxy-2-cyclohexenone (40.8 g) in THF (50 ml). The resulting solution was allowed to warm to ambient temperature. After a further 3 hours the cooled solution was treated with concentrated hydrochloric acid (120 ml) and stirred for 18 hours. The THF layer was combined with several chloroform extracts from the aqueous layer. Evaporation of the solvent gave a yellow solid, which was recrystallised from ethyl acetate to give hexahydro 3-(3-oxocyclohexen-1-yl) -2H-azepin-2-one as an off-white solid (45.5 g) m.p. 159°–165° C.

Analysis: Found: C, 68.9; H, 8.74; N, 6.74%: C$_{12}$H$_{17}$NO$_2$ requires C, 69.54; H, 8.27; N, 6.76%.

EXAMPLE 17

3-(3-Hydroxyphenyl)hexahydro-2H-azepin-2-one

A mixture of hexahydro-3-(3-oxocyclohexen-1-yl)-2H-azepin-2-one (20.73 g), cupric bromide (44.9 g) and lithium bromide (8.8 g) was refluxed in acetonitrile (1000 ml) for 1 hour. Evaporation of the solvent left a black gum which was triturated with an excess of 2 N sodium hydroxide solution. The resulting orange suspension was filtered through Kieselguhr, and the filtrate acidified (conc.HCl). The white suspension was extracted several times with chloroform, and the residue left on evaporation of the organic layers was crystallised from ethyl acetate to give 3-(3-hydroxyphenyl)-hexahydro-2$\underline{H}$-azepin-2-one (11.8 g) m.p. 175°–178° C.

Analysis: Found: C, 70.1; H, 7.6; N, 6.6%: C$_{12}$H$_{15}$NO$_2$ requires C, 70.22; H, 7.37; N, 6.82%.

EXAMPLE 18

3-(3-Benzyloxyphenyl)hexahydro-2$\underline{H}$-azepin-2-one

A solution of 3-(3-hydroxyphenyl)hexahydro-2H-azepin-2-one (2.05 g) in dry DMF was added dropwise to a suspension of sodium hydride (0.3 g). After 30 minutes at ambient temperature, benzyl chloride (1.3 g) was added. The mixture was stirred for a further 2 hours and then cooled, and treated with water. The resulting solution was extracted several times with toluene, and the combined toluene layers washed thoroughly with water. The solvent was evaporated to give an oil that crystallised from ethyl acetate to give the title compound as a white solid (1.4 g) m.p. 119°–122° C.

Analysis: Found: C, 77.42; H, 7.37; N, 4.64%: $C_{19}H_{21}NO_2$ requires C, 77.26; H, 7.17; N, 4.74%.

EXAMPLE 19

3-Ethyl-hexahydro-3-(methoxyphenyl)-2$\underline{H}$-azepin-2-one

Lithium diisopropylamide, prepared by adding 15% butyl lithium in hexane (15.7 ml) to diisopropylamine (3.15 ml) at −10° C. under nitrogen, was treated with a solution of hexahydro-3-(3-methoxyphenyl)-1-methyl-2H-azepin-2-one in THF. After 30 minutes, ethyl bromide (1.0 ml) was added. The mixture was allowed to warm to ambient temperature. After a further 2 hours the reaction was quenched with water. The organic layer was evaporated to give an oil that crystallised on scratching. The solid was recrystallised from ethyl acetate to give the title compound (1.68 g) m.p. 85°–87° C.

Analysis: Found: C, 72.88; H, 8.91; N, 5.39%: $C_{15}H_{21}NO_2$ requires C, 72.84; H, 8.56; N, 5.66%.

EXAMPLE 20

Hexahydro-3-(3-hydroxyphenyl)-1-phenylmethyl-2$\underline{H}$-azepin-2-one

A solution of hexahydro-1-phenylmethyl-2H-azepin-2-one (5.68 g) in dry THF was added at −10° C. to lithium diisopropylamide (0.032 mm) prepared from diisopropylamine (4.4 ml) and butyl lithium (22.9 ml of 1.4 M solution in hexane). The mixture was stirred for 30 minutes and then treated with a solution of 3-methoxy-2-cyclohexenone (2.53 g) in THF. After 5 hours at ambient temperature the mixture was poured onto ice-cold concentrated hydrochloric acid (100 ml). After vigorously stirring for 12 hours the solution was shaken with several portions of chloroform. The combined chloroform layers were evaporated to give an orange oil. This was refluxed with cupric bromide (8.95 g) and lithium bromide (1.74 g; 0.02 m) in acetonitrile for 1 hour. Removal of the solvent left a black oil that was triturated with excess 2 N sodium hydroxide solution. The filtrate, after removal of the orange precipitate, was extracted with methylene chloride. The organic layer was acidified (conc.HCl) and the white suspension shaken with several portions of chloroform and were evaporated to leave a dark red oil (1.2 g) that crystallised from ethyl acetate to give the title compound (0.35 g) m.p. 160°–166° C.

Analysis: Found: C, 75.31; H, 7.48; N, 4.36%. $C_{19}H_{21}NO_2\cdot\frac{1}{2}H_2O$ requires C, 74.97; H, 7.28; N, 4.6%.

EXAMPLE 21

Hexahydro-3-(3-hydroxyphenyl)-1-methyl-2$\underline{H}$-azepin-2-one

A solution of hexahydro-1-methyl-3-(3-oxocyclohexen-1-yl)-2H-azepin-2-one (150 g) in dichloromethane (750 ml) was warmed to 25° C. Bromine (97.5 g) was added over 40 minutes at 25°–32° C. (occasional water cooling being applied) and the mixture stirred for 2 hours at about 25° C. Water (200 ml) was added and the dichloromethane layer washed with water (100 ml). The aqueous phases were combined and extracted into dichloromethane (2×100 ml). The dichloromethane extracts were combined and the solvent distilled off and replaced with ethyl acetate to keep temperature of 72° C. (750 ml ethyl acetate added; 90 ml distillate collected). The mixture was cooled to room temperature and filtered. The product was washed with 100 ml ethyl acetate and dried to give the title compound (134.3 g) as a crystalline fawn powder, m.p. 184°–189° C. Identical to product of Example 4.

EXAMPLE 22

Hexahydro-3-(3-oxocyclohexen-1-yl)-2$\underline{H}$-azepin-2-one

Butyllithium (143 ml of 1.4 molar solution in hexane) was added dropwise to a stirred solution of caprolactam (11.3 g) in dry tetrahydrofuran under nitrogen. After stirring for 50 minutes at 0°, 3-methoxy-2-cyclohexenone (12.6 g) in tetrahydrofuran was added. After a further 30 minutes the reaction was poured onto 5 M hydrochloric acid. The organic layer was separated and the aqueous layer was extracted with chloroform. The combined organic layers were dried over magnesium sulphate. Removal of the solvent under reduced pressure left 15 g of a yellow solid. The product was recrystallised from ethyl acetate affording 2.5 g of the title compound identical to that described in Example 17.

EXAMPLE 23

Hexahydro-3-(3-methoxyphenyl)-2$\underline{H}$-azepin-2-one

A suspension of hexahydro-3-(3-hydroxyphenyl)-2H-azepin-2-one (4.1 g), anhydrous potassium carbonate (5.6 g) and dimethyl sulphate (2.52 g) was heated under reflux with stirring in acetone (50 ml). After cooling the solution was filtered and evaporated to dryness under reduced pressure. The product was recrystallised from diisopropyl ether/ethyl acetate affording the title compound, identical to that obtained by the method of Example 1.

EXAMPLE 24

3-Ethylhexahydro-3-(3-methoxyphenyl)-2$\underline{H}$-azepin-2-one

Hexahydro-3-(3-methoxyphenyl)-2H-azepin-2-one (2.19 g) in dry tetrahydrofuran was added to a stirred solution of lithium diisopropylamide (from butyllithium 1.4 molar 15.7 ml, and diisopropylamine 3.15 ml) under nitrogen at 0° C. Ethyl bromide (1 ml) was added in one portion and the reaction allowed to warm up to room temperature. After two hours the reaction was poured into 2 M HCl, the organic layer separated and the aqueous layer extracted with chloroform. The combined organic layers were dried over magnesium sulphate, filtered and evaporated to an oil which was crystallised from ethyl acetate giving 1.68 g of the title compound m.p. 85°–7° C.

Analysis: Found: C, 72.0; H, 8.9; N, 5.4%: $C_{15}H_{21}NO_2$ requires C, 72.8; H, 8.6; N, 5.7%.

EXAMPLE 25

3-n-Butyl-hexahydro-3-(3-hydroxyphenyl)-1-methyl-2$\underline{H}$-azepin-2-one 3-(3-hydroxyphenyl)-1-methyl-hexahydro-2$\underline{H}$-azepin-2-one (11 g) as a finely powdered solid was added portionwise to a solution of lithium diisopropylamide (from diisopropylamine 14.8 ml, and 77 ml of 1.4 M butyllithium) in dry tetrahydrofuran (500 ml) under nitrogen. The suspension was heated under reflux for 3 hours, and n-bromobutane (5.6 ml, 7.14 g) added. The reaction was heated under reflux for a further 6 hours, cooled to 0° C. and an excess of 5 M hydrochloric acid added slowly dropwise. The organic layer was separated and the aqueous layer extracted with chloroform. The combined organic extracts were washed with saturated sodium chloride, dried with magnesium sulphate and evaporated to an oil. The oil was crystallised and recrystallised from ethylacetate, affording 9.5 g of colourless crystals m.p. 138°–142° C.

Analysis: Found: C, 74.05, H, 9.52, N, 4.58%: $C_{17}H_{25}NO_2$ requires C, 74.1; H, 9.5; N, 5.1%.

We claim:

1. A compound of formula (I)

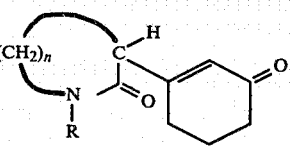

wherein n is 2,3 or 4 and R is hydrogen, lower alkyl phen(lower)alkyl or substituted phen(lower)alkyl, wherein the substituent is selected from halogen, lower alkoxy and trifluoromethyl.

2. A compound as claimed in claim 1 wherein R is hydrogen, lower alkyl or benzyl.

3. A compound as claimed in claim 1 wherein n is 4.

4. A compound as claimed in claim 1 which is hexahydro-1-methyl-3-(3-oxocyclohexen-1-yl)-2H-azepin-2-one.

5. A compound as claimed in claim 1 which is 1-methyl-3-(3-oxocyclohexen-1-yl)-2-piperidone.

6. A compound as claimed in claim 1 which is 1-methyl-3-(3-oxocyclohexen-1-yl)-2-pyrrolidone.

7. A compound as claimed in claim 1 which is hexahydro-3-(3-oxocyclohexen-1-yl)-2H-azepin-2-one.

8. A compound as claimed in claim 1 which is hexahydro-1-phenylmethyl-3-(3-oxocyclohexen-1-yl)-2H-azepin-2-one.

9. A compound of the formula

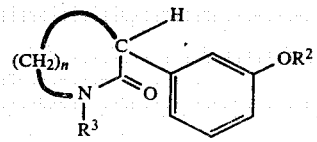

wherein n is 2,3 or 4, $R^2$ is hydrogen, lower alkyl phen(lower)alkyl or substituted phen(lower)alkyl wherein the substituent is selected from halogen, lower alkoxy and trifluoromethyl and $R^3$ is hydrogen, lower alkyl, lower alkenyl, lower alkynyl, or phen(lower)alkyl or substituted phen(lower)alkyl wherein the substituent is selected from halogen, lower alkoxy and trifluoromethyl.

10. A compound as claimed in claim 9 wherein $R^3$ is hydrogen, lower alkyl, phen(lower)alkyl or substituted phen(lower)alkyl, wherein the substituent is selected from halogen, lower alkoxy and trifluoromethyl.

11. A compound as claimed in claim 9 wherein n is 4.

12. A compound as claimed in claim 10 which is hexahydro-3-(3-methoxyphenyl)-2H-azepin-2-one.

13. A compound as claimed in claim 10 which is hexahydro-3-(3-methoxyphenyl)-1-methyl-2H-azepin-2-one.

14. A compound as claimed in claim 10 which is hexahydro-3-(3-hydroxyphenyl)-1-methyl-2H-azepin-2-one.

15. A compound as claimed in claim 10 which is 3-(3-hydroxyphenyl)-1-methyl-2-piperidone.

16. A compound as claimed in claim 10 which is 3-(3-hydroxyphenyyl)-1-methyl-2-pyrrolidone.

17. A compound as claimed in claim 10 which is 3-(3-hydroxyphenyl)hexahydro-2H-azepin-2-one.

18. A compound as claimed in claim 10 which is 3-(3-benzyloxyphenyl)hexahydro-2H-azepin-2-one.

19. A compound as claimed in claim 10 which is hexahydro-3-(3-hydroxyphenyl)-1-phenylmethyl-2H-azepin-2-one.

* * * * *

UNITED STATES PATENT AND TRADEMARK OFFICE
CERTIFICATE OF CORRECTION

PATENT NO. : 4,197,241
DATED : April 8, 1980
INVENTOR(S) : J. F. Cavalla et al

It is certified that error appears in the above-identified patent and that said Letters Patent are hereby corrected as shown below:

Page 1, under the foreign application priority data should read -- 53370/77 -- for "33370/77".

Column 7, line 58 should read - Hexahydro- -- for "Hexahydro-b";

Column 12, line 51 should read -- 11.18 -- for "11.8";

Column 15, line 19 should read -- lower alkyl, -- for "lower alkyl";

Column 16, line 9 should read -- lower alkyl, -- for "lower alkyl".

Signed and Sealed this

Twenty-fourth Day of February 1981

[SEAL]

Attest:

RENE D. TEGTMEYER

Attesting Officer

Acting Commissioner of Patents and Trademarks